(12) United States Patent
Naffakh et al.

(10) Patent No.: US 7,935,807 B2
(45) Date of Patent: May 3, 2011

(54) CHICKEN RNA POLYMERASE I PROMOTER AND THE USE THEREOF

(75) Inventors: Nadia Naffakh, Malakoff (FR); Pascale Massin, Saint Brieuc (FR); Sylvie Van Der Werf, Gif-sur-Yvette (FR)

(73) Assignees: Institut Pasteur, Paris (FR); Centre National de la Recherche Scientifique (SNRS), Paris (FR); Universite Paris 7-Denis Diderot, Paris (FR)

( * ) Notice: Subject to any disclaimer, the term of this patent is extended or adjusted under 35 U.S.C. 154(b) by 1279 days.

(21) Appl. No.: 10/547,155

(22) PCT Filed: Feb. 27, 2004

(86) PCT No.: PCT/FR2004/000460
§ 371 (c)(1),
(2), (4) Date: Jul. 10, 2006

(87) PCT Pub. No.: WO2004/078912
PCT Pub. Date: Sep. 16, 2004

(65) Prior Publication Data
US 2007/0134270 A1    Jun. 14, 2007

(30) Foreign Application Priority Data

Feb. 28, 2003    (CA) ..................................... 2421086

(51) Int. Cl.
*C07H 21/04* (2006.01)
*G01N 33/48* (2006.01)

(52) U.S. Cl. ........................................ 536/24.1; 435/94

(58) Field of Classification Search ........................ None
See application file for complete search history.

(56) References Cited

U.S. PATENT DOCUMENTS 6,610,836 B1 *    8/2003    Breton et al. ................. 536/23.1
7,214,786 B2 *    5/2007    Kovalic et al. ............... 536/23.6

FOREIGN PATENT DOCUMENTS

WO    WO 99/13886 A1 *    3/1999
WO    WO 03/008540 A2 *    1/2003

OTHER PUBLICATIONS

Chen et al. Mol Cell Biol. Oct. 2003; 23(20): 7350-7362.*
Willige et al. J. Thromb. Haemost. Jun. 2007; 5(6):1243-1249.*
Orkin et al "Report and Recommendation of the Panel to Assess the NIH Investment in Research on Gene Therapy", Dec. 7, 1995. pp. 1-37.*
Houdebine et al. Journal of Biotechnology, 1994, vol. 34, pp. 269-287.*
Guillemot, F. et al., "A Molecular Map of the Chicken Major Histocompatibility Complex: The Class II β Genes are Closely Linked to the Class I Genes and the Nucleolar Organizer," The EMBO Journal, vol. 7, No. 9, pp. 2775-2785, (1988).
Neumann, G. et al., "Generation of Influenza A Viruses Entirely form Clones cDNAs," Proc. Natl. Acad. Sci, USA, vol. 96, pp. 9345-9350, (Aug. 1999).
Schmid, M. et al., "First Report on Chicken Genes and Chromosomes 2000," Cytogenet Cell Genet, vol. 90, pp. 169-218, (2000).
Neumann, G. et al., "Reverse Genetics of Influenza Virus," Virology, vol. 287, pp. 243-250, (2001).
Gross, T. A. et al., "The Efficacy of Influenza Vaccine in Elderly Persons: A Meta-Analysis and Review of the Literature," Annals of Internal Medicine, vol. 123, No. 7, pp. 518-527, (Oct. 1, 1995).
Keitel, W. A. et al., "Live Cold-Adapted, Reassortant Influenza Vaccines," Textbook of Influenza, Chapter 28, pp. 373-390, Blackwell Science, Ltd., Oxford, England, (1998).
Fodor, E. et al., "Rescue of Influenza A Virus from Recombinant DNA," Journal of Virology, vol. 73, No. 11, pp. 9679-9682, (Nov. 1999).
Hoffmann, E. et al., "A DNA Transfection System for Generation of Influenza A Virus from Eight Plasmids," PNAS, vol. 97, No. 11, pp. 6108-6113, (May 23, 2000).
Heix, J. et al., "Species Specificity of Transcription by RNA Polymerase I," Current Opinion in Genetics & Development, vol. 5, pp. 652-656, (1995).
Grosveld, F. G. et al., "The Construction of Cosmid Libraries which can be Used to Transform Eukaryotic Cells," Nucleic Acids Research, vol. 10, No. 21, pp. 6715-6732, (1982).
Pleschka, S. et al., "A Plasmid-Based Reverse Genetics System for Influenza A Virus," Journal of Virology, vol. 70, No. 6, pp. 4188-4192, (Jun. 1996).
Paule, M. R., "Promoter Structure of Class I Genes," Transcription of Ribosomal RNA Genes by Eukaryotic RNA Polymerase I, Springer-Verlag and R.G. Landes Company, pp. 39-50, (1998).
Manuguerra, J. C., "Vaccination Anti-Grippale: État De La Question," Repères sur Les Infections Brocho-Pulmonaires, P. Léophonte & Y. Mouton: PIL, pp. 328-342, (2001).

* cited by examiner

*Primary Examiner* — Bao Li
(74) *Attorney, Agent, or Firm* — Finnegan, Henderson, Farabow, Garrett & Dunner LLP (57) ABSTRACT

The invention relates to a novel polynucleotide exhibiting a promoting transcription activity, polynucleotide-containing vectors and to the use thereof for the transcription of interesting sequences such as the production of non-cap RNA virus. Said invention also relates to host cells preferably of avian origin, containing a polynucleotide or the inventive vector.

21 Claims, 6 Drawing Sheets

CCGGTGGTCCCGGCCCCGTCCGACTCGGTCGCTTCGCGGAGGTGGCTGGAGGTCGCTGCC

GTGGCGGCTGGGGCACGGCGGAACGGTCTAACCGGCTCCGGCGGGCCCCGTCCGCCTCGG

TCGCTGCTCGGCGGCTGCTAGGGGTCGCTGCCGGGGTGGCTGGGGCACGGCGGAACGGTC

TACCCGGGTCCGGCGGGCGCCGTCCGGCTCGGTCGCTCCGCGGAGGAGGCTAGGGGTCGC

TGCCGGGGCGTCTCGGAAACGGCGGAACGGTCTACCCGGCTCCGGCGGGCCCCGTCCGCC

TCGGTCGCTCCGCGCCGGCGGCGGCTAGAGGTCGCTGCCGTGTCGGCTCGGAAACGGCGG

AACGGTCTACCCGGCTCCGACGGGCGCCGTCCGGCTCGGTAGCTCCGCGGCGGCGGCTAG

AGGTCGCTGCCGTGTCGGCTCGGAAACGGCGGAACGGTCTACCCGGCTCCGGCGGGCGCC

GTCCGGCTCGGTCTCTCCGCGGCGGCGGCTAGAGGTCGCTGCCGTGTCGGCTCGGAAACG

GCGGAACGGTCTACCCGGGTCCGACGGGCGCCGTCCGGCTCGGTCTCTCCGCGGCGGCGG

CTAGAGGTCGCTGCCGTGTCGGCTCGGAAACGGCGGAACGGTCTACCCGGCTCCGACGGG

CCCCGTCCGGCTCGGTCGCTCCGCGGCGGCGGCTAGGGGTCGCTGCCGGGGCGTCTCGGA

AACGGCGGAACGGTCTACCCGGGTGCTACCGACTCGCGCTCTCCGCGGCGGCGGCTAGAG

GTCGCTGCCGGGGCGGCTTGCGATCCGCGTCCAGGTCTACCCGGTTTCGGATTGTCTTGG

CCGCTCTGGCTGTGGGGGGGGCGCTACAGCTCCGGAGCTGCCAGAGGCGTCGCTGTAAT

TTTGTACCTCCAGTTACGTCGAGGTAAACCTCGGCTGCCGTCGGAGCCGCTGCCGGTAGT

CGGCGCCTATGGGGCTAGAACGTTTTTTTCGGATGCCTTATATGTTCGTCTGTAGGAGCG

AGTGAGGACTCGGCTCCGGTAGTGGCGGTGAGCGGGCGCTCGCGAGCAGGGTTGACCGGC

CGGCCGCCTAGAGAGGGGATCGGCGGCGGCGGCGGCGGCTTTCTCGGGCATCGGTTCGTT

CGATCGGTCCGGTCGCTTCGGTTTGTCCGTCGCTCCTCATCCCGCAGCTCTGTCCTGGGC

TAAGGCGGTTTTGCAGGCGAGCAGCGAAAAAAGCCGGAGAAGGCGATCACTAGTGCGGC

```
TCCGCGGCGGCGGCTAGAGGTCGCTGCCGTGTCGGCTCGGAAACGGCGGAACGGTCTACC

CGGCTCCGACGGGCCCCGTCCGGCTCGGTCGCTCCGCGGCGGCGGCTAGGGTCGCTGCC

GGGGCGTCTCGGAAACGGCGGAACGGTCTACCCGGGTGCTACCGACTCGCGCTCTCCGCG

GCGGCGGCTAGAGGTCGCTGCCGGGGCGGCTTGCGATCCGCGTCCAGGTCTACCCGGTTT

CGGATTGTCTTGGCCGCTCTGGCTGTGGGGGGGGCGCTACAGCTCCGGAGCTGCCAGAG

GCGTCGCTGTAATTTTGTACCTCCAGTTACGTCGAGGTAAACCTCGGCTGCCGTCGGAGC

CGCTGCCGGTAGTCGGCGCCTATGGGGCTAGAACGTTTTTTCGGATGCCTTATATGTTC

GTCTGTAGGAGCGAGTGAGGACTCGGCTCCGGTAGTGGCGGTGAGCGGGCGCTCGCGAGC

AGGGTTGACCGGCCGGCCGCCTAGAGAGGGGATCGGCGGCGGCGGCGGCGGCTTTCTCGG

GCATCGGTTCGTTCGATCGGTCCGGTCGCTTCGGTTTGTCCGTCGCTCCTCATCCCGCAG

CTCTGTCCTGGGCTAAGGCGGTTTTGCAGGCGAGCAGCGAAAAAAGCCGGAGAAGGCGA

TCACTAGTGCGGCC
```

FIGURE 2

|  | pTCF-CAT | pTCF (PacI.NotI)-CAT |
|---|---|---|
|  | ↓ | ↓ |

Day 1 • Transfection of QT6 cells with Fugene (Roche)

Day 2 • RNA extraction from cells transfected with Trizol (GibcoBRL)

• Treatment of RNA with DNAase-free RNase (Ambion) 2 times 1h at 37°C with 8U of enzyme

• Phenol-CHCl₃ extraction, precipitation of RNA in ethanol, recovery of aliquots of RNA in water p.p.t.

• Measure concentration by absorbance at 260 nm

Day 3 • Deposit 5 µg of RNA Hybond N+ membrane using a Slot-Blot apparatus (Hoefer Scientific Instrument)

• Hybridize with a CAT riboprobe complementary to the CAT strand likely to be transcribed, synthesized by the phage T7 or SP6 polymerase (Promega) en présence de $\propto^{32}$P.rUTP (Amersham), purified on QIAGEN columns (PCR Purification Kit)

Hybridization buffer:
Hybridization conditions: overnight at 65°C in a hybridization incubator (Amersham Life Sciences)

Day 4 • Washes

• Exposure to a PhosphoImager screen (Molecular Dynamics), Scanning with the PhosphoImager

• Quantification of signals the software Dmage Quart (Molecular Dynamics)

pTCF        pTCF (PacI-NotI)
CAT         CAT

FIGURE 3

Vectors 1 = C13-18, 2 = pTCF (PacI-NotI)-CAT, 3 = pTCF (PacI-NotI) ? (SfiI-NotI)-CAT,
4 = pTCF (PacI-NotI) ? (PacI-SfiI)-CAT, 5 = pGEM (SacI-NotI)-CAT,
6 = pGEM (SfiI-SacI)-CAT, 7 = pGEM (SmaI-900)-CAT, 8 = pGEM (SmaI-300)-CAT,
9 = pGEM (AgeI-1000)-CAT, 10 = pGEM (SfiI-SacI)-) ? (AgeI)- CAT,
11 = pGEM (SfiI-AgeI)-CAT, 12 = pGEM (AgeI-SacI)-CAT

CHICKEN RNA POLYMERASE I PROMOTER AND THE USE THEREOF

The present invention relates to a novel polynucleotide that possesses a transcription-promoting activity, to vectors containing this polynucleotide, and to the use thereof for the transcription of sequences of interest, such as for the production of uncapped viral RNA. The present invention also relates to host cells, preferably of avian origin, that contain a polynucleotide or a vector in accordance with the invention.

The prevention of influenza rests primarily on vaccination, which is strongly recommended. In France, for example, 100% of the cost of vaccination is covered by the French national health insurance agency for persons at risk, which are primarily those subjects 65 years of age and older and subjects suffering from chronic respiratory, cardiovascular, renal, and metabolic afflictions. Post-vaccine immunity is conferred by the production of antibodies directed against surface glycoproteins, in particular against hemagglutinin (HA) but also against neuraminidase (NA).

I—Current Methods: Production Using Fertilized Chicken Eggs and Inactivation

Influenza vaccines are composed of three different virus strains: two Type A (H3N2 and H1N1) and a Type B. The choice of vaccine strains is reevaluated each year in accordance with the monitoring data for the variations in circulation, and is the subject of a WHO recommendation which is announced in mid-February for the northern hemisphere. The vaccines used today, as they have been for the last thirty years, are composed of viruses reproduced in fertilized chicken eggs and then inactivated (Manuguerra, 2001, *Repères sur les infections bronchopulmonaires*, pp. 328-342. Edited by P. Léophonte & Y. Mouton: PIL).

For Type A viruses, reassortant viruses with high reproduction capacities in fertilized eggs and with the HA and NA of the variations indicated by the WHO are prepared and provided to the industrial vaccine producers. One or two fertilized eggs are required to manufacture a dose of trivalent vaccine. Each vaccine manufacturer performs the purification step differently, but all follow the same principle: allantoic fluid is taken and the viruses are inactivated by treatment with formaldehyde or β-propiolactone before being purified by ultracentrifugation. The viruses may be fragmented using lipid and/or detergent solvents such as Tween 80. The whole or fragmented viruses are then adjusted to the standard level of 15 μg of HA per dose of vaccine, per strain. A purification step in the presence of dialyzable detergent makes it possible to produce a subunit vaccine that contains nothing more than the envelope glycoproteins (HA and NA) of the virus. Because of the stronger reactogenicity of vaccines that contain whole viruses, it is in fact the fragmented and subunit vaccines which are marketed today. The period necessary for a vaccine to be produced and quality tested in conformity with European standards before its release on the market is about 6 months.

Comprised of inactivated viruses, influenza vaccines are generally very well tolerated and cause only minor adverse reactions, such as local reactions at the point of injection and febrile reactions and cephalgias in the 48 hours following injection. The contraindications for influenza vaccination are limited to allergies to egg proteins, primarily egg albumin, and to allergies to manufacturing residues or mercurothiolate. In the absence of information on the effects which it may have on fetal development, influenza vaccination is not recommended for women in the first trimester of pregnancy.

The protective effectiveness of a vaccine comprised of inactivated viruses against a subsequent influenza infection is difficult to evaluate because the effectiveness may vary widely from one season to another, in particular as a function of the degree of the antigenic relationship between the circulating viruses and those included in the vaccine, and because effectiveness also depends on the state of immunization of the vaccinated person. In France, the improvement in vaccine coverage between 1979 and 1999 was accompanied by a reduction in influenza-related mortality (approximately 20,000 deaths per year in 1979; 2,500 deaths per year since 1985), which suggests, if not demonstrates, a positive impact by vaccine policy. In addition, evidence from a number of studies makes it possible to estimate that vaccinations for the elderly can decrease the number of viral pneumonias and hospitalizations by half and the number of fatal influenza cases by about seventy percent (Large et al., 1995, Annals of Internal Medicine, 123, 518-527).

II—Developmental Prospects for Influenza Vaccines

Several avenues of research are currently under investigation for the purpose of 1) improving the intensity, quality, and duration of responses induced by influenza vaccines, and enlarging their specificities; and 2) allowing a rapid response should a virus of a potentially pandemic sub-type emerge. Work concerning the production of live vaccines as well as the production of vaccine viruses in cell cultures are summarized below. Among the other avenues of research explored, the use of adjuvants, recombinant subunit vaccines, and polynucleotide vaccines should also be noted.

—Production of Live Vaccines

A live influenza vaccine is likely to induce a broader and longer-lasting immunity because, in particular, it stimulates immunity via cellular mediation. A live vaccine is also likely to be better accepted by the general population because it is administered by the nasal, and not parenteral, route. Two types of live vaccines can be envisaged today: live attenuated vaccines and live recombinant vaccines.

Live Attenuated Vaccines

Attenuated strains are obtained by the reassortment of circulating wild strains with a donor strain that has been attenuated by cold adaptation and whose genotype is well characterized, however without perfect establishment of the relationships between the mutations observed and the phenotype (attenuation, cold adaptation, heat-sensitivity) (Keitel et al., 1998, Textbook of Influenza, pp. 373-390. Edited by K. G. Nicholson, R. G. Webster & A. J. Hay. Oxford, England: Blackwell Science, Ltd.).

The method for producing attenuated vaccines in fertilized chicken eggs is analogous to that described above, but without the virus inactivation step. The results of clinical tests conducted recently by American researchers indicate that trivalent vaccines comprised of attenuated strains administered by intranasal route are harmless for adults, the elderly, and children, with only throat irritation and nasal discharge during the 48 hours following vaccination as side effects. They may have greater protective efficacy than inactivated vaccines, particularly due to the induction of an IgA antibody mucosal response, but their transmission and reversion potentials remain to be documented. Vaccination with live attenuated viruses has been practiced widely in Russia for several decades, but it is difficult to draw convincing overall conclusions because of the variety of conditions employed.

Live Recombinant Vaccines

The recent development of reverse genetics systems for influenza viruses (Neumann et al., 2001, Virology 287, 243-50) makes it possible to envisage the production of recombinant viruses in the genome with genetic modifications specifically introduced in order to confer properties of adequate attenuation and immunogenicity. This approach offers increased security (because of the absence of contaminating agents such as those which may introduced when viral strains are sampled and the possibility of more easily minimizing and controlling the risks-of reversion of the vaccine virus) and would make it possible to respond more specifically to varied epidemic situations. The reverse genetics systems in existence today are based on the use of the human RNA polymerase I transcription system. Because of the narrow species specificity of RNA polymerase I, its use is restricted to cells of human or primate origin. It can be used for the production of recombinant vaccine viruses in cell cultures but not in fertilized chicken eggs.

—Production of Vaccine Viruses in Cell Cultures

The principal advantages of using fertilized chicken eggs in the production of vaccine influenza viruses are: i) a greatly increased virus yield; and ii) a minimum risk of contamination by agents pathogenic to man, a particular consideration in the production of non-inactivated vaccines. The possibility of producing vaccine viruses in cells cultivated in a medium lacking serum is also explored. The companies Baxter and Solvay recently approved banks of cells derived from the Vero and MDCK lines, respectively, for the production of vaccine viruses. A vaccine produced in MDCK cells and inactivated received marketing authorization in 2001 but has yet to be commercialized.

Several types of influenza vaccines, both inactivated and live, and both those produced in fertilized chicken eggs and those produced in cell cultures, will likely coexist in the future marketplace. Among these some may appear particularly indicated for the vaccination of a certain category of subjects, and less indicated for the vaccination of another category. In the event of a pandemic, all production means available, using fertilized eggs and cell cultures, will need to be mobilized.

The present invention responds to these needs and other needs as will be apparent to the skilled reader of the present description of the invention.

The present invention relates to a polynucleotide, to recombinant DNA that contain the aforesaid polynucleotide, and to the use thereof, preferably for the production of uncapped RNA viruses to be used in a vaccine.

Figure 1:
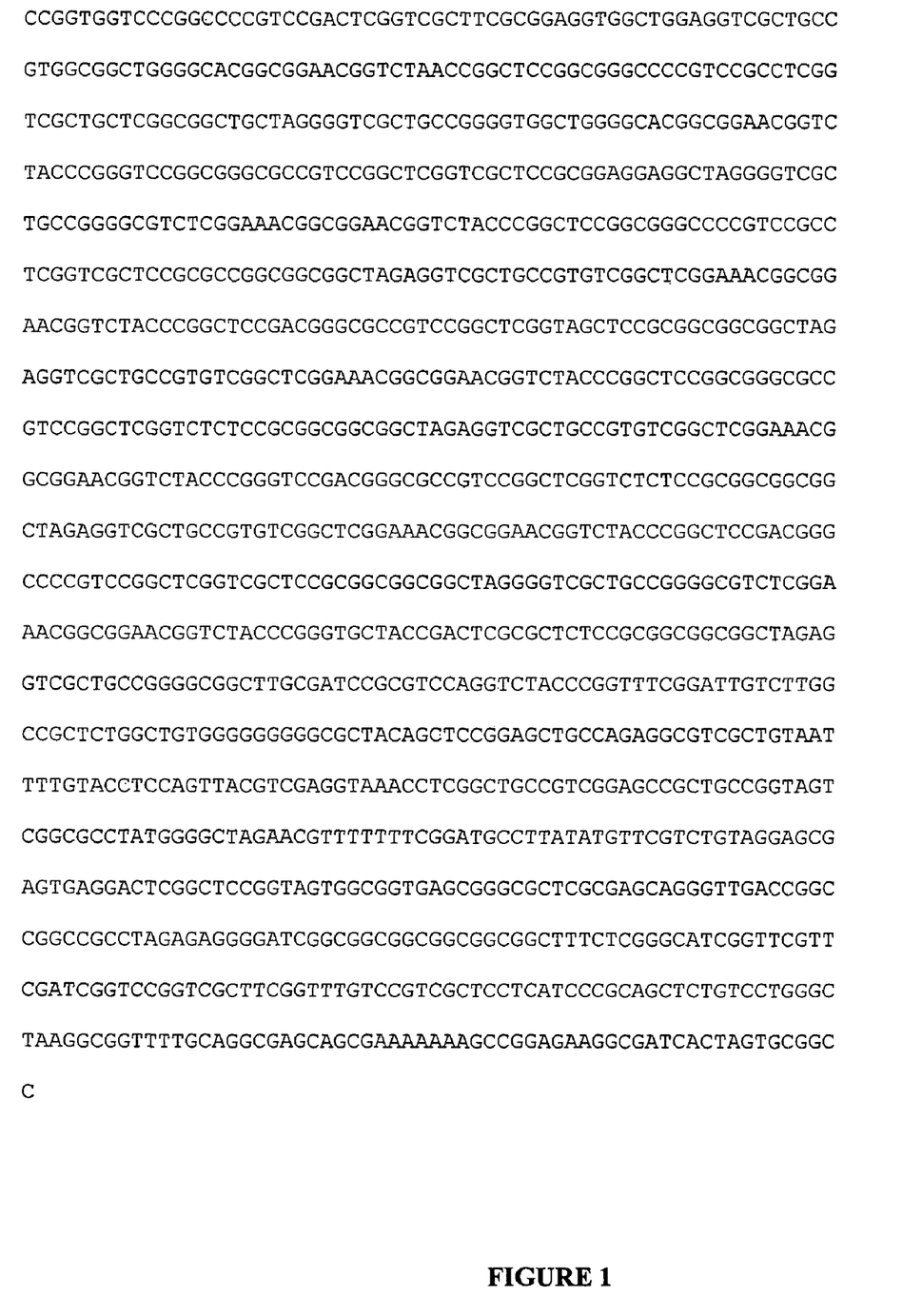
FIG. 1 shows a sequence (SEQ ID NO: 1) that corresponds to the AgeI-SacI chicken genomic DNA fragment which contains the chicken RNA polymerase I promoter.

More specifically, the present invention has as an aim an isolated or purified polynucleotide which includes sequence SEQ ID NO: 1, presented in FIG. 1, or a fragment thereof, which preferably has a transcription-promoting activity.

Figure 2:
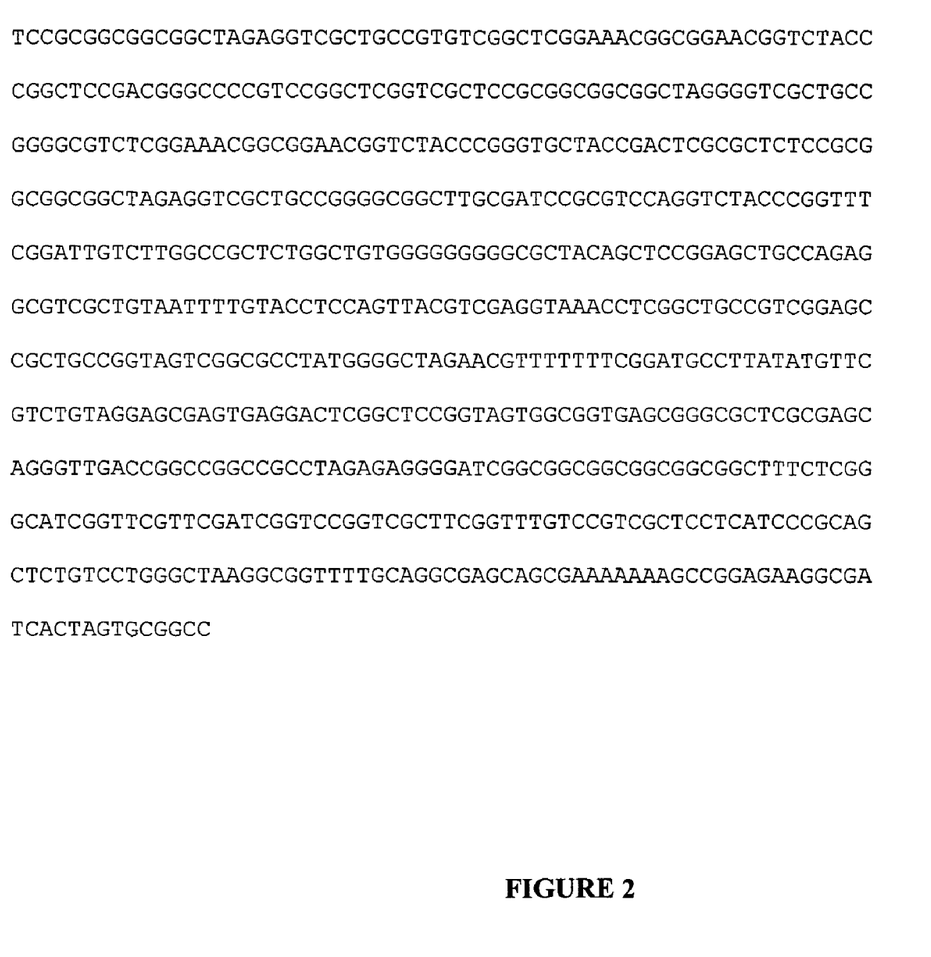
FIG. 2 shows a second fragment of chicken genomic DNA (BsaI-SacI) of sequence SEQ ID NO: 2 which contains the chicken RNA polymerase I promoter.

The present invention also relates to an isolated or purified polynucleotide that includes sequence SEQ ID NO: 2, presented in FIG. 2, or a fragment thereof, which preferably has a transcription-promoting activity.

The invention also relates to: a recombinant DNA that includes one of the polynucleotides in accordance with the invention, or a fragment thereof; a vector that includes one of the polynucleotides in accordance with the invention, or a recombinant DNA, or a fragment of recombinant DNA; a host cell and a fertilized egg of avian origin that contains a polynucleotide and/or a recombinant DNA in accordance with the invention.

The invention also relates to the use of at least one of the following elements for the production of a sequence of interest such as, for example, an uncapped recombinant RNA virus:
 a polynucleotide in accordance with the invention;
 a recombinant DNA in accordance with the invention;
 a vector in accordance with the invention;
 a host cell in accordance with the invention; and
 a fertilized egg of avian origin in accordance with the invention.

In a specific embodiment, the invention relates to a method for the production of uncapped recombinant viruses by reverse genetics, wherein the method comprises the following steps:
 a) introducing one or several vectors into a cell or fertilized egg of avian origin, the aforesaid vector or vectors comprising a recombinant DNA in accordance with the invention, and the DNA that express the proteins necessary for the transcription/replication of viral RNA;
 b) applying to the cell or egg obtained in a) conditions that make possible the expression of recombinant viruses; and
 c) recovering the recombinant viruses obtained in b).

In a preferred embodiment, the present invention proposes a method for the production of recombinant influenza viruses by reverse genetics, wherein the method comprises the following steps:
 a) introducing into an avian cell or fertilized chicken egg at least one vector that comprises a recombinant DNA provided by a preferred method of the invention, and vectors that express the PA, PB1, PB2, and NP proteins of an influenza virus;
 b) applying to the cell or egg obtained in a) conditions that make possible the expression of recombinant influenza viruses; and
 c) recovering the recombinant influenza viruses obtained in b).

An aim of the invention is a compound that includes a pharmaceutically acceptable vehicle and a recombinant virus produced by a method in accordance with the present invention.

A particular aim of the, invention is an anti-influenza compound that includes a pharmaceutically acceptable vehicle and a recombinant influenza virus produced by a production method in accordance with the present invention.

The present invention also relates to a therapeutic compound that includes a sequence transcribed by a polynucleotide in accordance with the invention.

Advantageously, cloning the chicken RNA polymerase I promoter makes it possible to develop a reverse genetics system adapted to the production of recombinant vaccine viruses in fertilized chicken eggs, a system which may prove particularly well adapted to the production of live vaccines.

The invention also relates to the production of transgenic birds that express, under the control of the PolI promoter, RNA that confer resistance to infections by pathogenic microorganisms, in particular resistance to avian influenza viruses.

2. Cells and Fertilized Eggs of Avian Origin

In another aspect, the invention relates to cells transformed by a polynucleotide, and/or a recombinant DNA, and/or a vector as previously described. Preferably, the host cell thus transformed is of avian origin. In accordance with a preferred variation of the invention, the host cell is a poultry cell, and even more preferably a chicken cell. It is understood that in the sense of the present invention the host cells are transformed in a steady manner. However, it is possible to provide transformed cells in a transitory manner.

In a related aspect, the present invention also relates to "transfected" fertilized eggs of avian origin (preferably from hens). More particularly, the fertilized eggs of the present invention include a polynucleotide, and/or a recombinant DNA, and/or a vector as previously described.

The methods employed to introduce, into a host cell or fertilized egg, a polynucleotide, and/or a recombinant DNA, and/or a vector as previously described, in accordance with the present invention, is based on the general knowledge of a professional in the fields of cellular transfection and egg incubation, and thus these methods will not be described in greater detail.

3. Methods and Procedures

In accordance with another aspect, the invention relates to the production of sequences of interest such as, for example, recombinant vaccine viruses, and more particularly to the production of an uncapped recombinant RNA virus. In an additional aspect, the invention targets the use of at least one of the following elements for the production of a sequence of interest, of an uncapped recombinant RNA virus, for example:
- a polynucleotide in accordance with the invention;
- a recombinant DNA in accordance with the invention;
- a vector in accordance with the invention;
- a host cell in accordance with the invention; and
- a fertilized egg of avian origin in accordance with the invention.

In a related aspect, the present invention proposes a method for the production of uncapped recombinant viruses. Such production is based on a reverse genetics system of recombinant virus production as previously described. More particularly, the method in accordance with the present invention comprises the following steps:
a) introducing into a cell or fertilized egg of avian origin one or several vectors, the aforesaid vector or vectors comprising a recombinant DNA in accordance with the invention, and the DNA that express the proteins necessary for transcription/replication viral RNA (such as proteins PA, PB1, PB2, and NP of an influenza virus, for example);
b) applying to the cell or egg obtained in a) conditions that make possible the expression of recombinant viruses; and
c) recovering the recombinant viruses obtained in b).

It will be understood that in step a) all DNA (recombinant DNA in accordance with the invention, and the DNA that express the proteins necessary to transcribe/replicate viral RNA) can be carried by a single vector, or two vectors, or more.

In a preferred embodiment, the present invention also proposes a method for the production of recombinant influenza viruses which comprises the following steps:
a) introducing into an avian cell or fertilized chicken egg at least one vector comprising preferentially a recombinant DNA that expresses an influenza virus vRNA and vectors that express proteins PA, PB1, PB2, and NP of an influenza virus such as, preferably, Type A influenza;
b) applying to the cell or egg obtained in a) conditions that make possible the expression of recombinant influenza viruses; and
c) recovering the recombinant influenza viruses obtained in b).

It will be understood that step c) of the methods in accordance with the invention, which comprises the recovery of the recombinant viruses, may take place directly in the cells, after cell lysis, or perhaps from the supernatant. If fertilized eggs are used, a person skilled in the art will know which methods to use in order to recover the recombinant viruses thus produced.

4. Composition

The present invention also relates to the use of these polynucleotides and recombinant DNA, and/or vectors that contain them, for the preparation of a composition to be used as vaccines. More specifically, a composition in accordance with the present invention includes, moreover, a sequence transcribed by a previously described polynucleotide. In a preferred embodiment, the present invention relates to the use of recombinant viruses for the preparation of vaccine compositions.

In another preferred embodiment, the composition of the present invention contains, moreover, a pharmaceutically acceptable vehicle and a recombinant virus obtained by a production method in accordance with the present invention.

The compositions in accordance with the present invention may take on the typical solid or liquid forms used for pharmaceutical administration, which is to say, for example, forms of administration including liquid, gel, or any other medium that permits, for example, controlled release. Among the compositions which may be used, of particular note are the injectable compositions specifically intended for injections into the human circulatory system.

A person skilled in the art will be able to prepare pharmaceutically acceptable compositions and to determine, as a function of several factors, the favored method of administration and the quantity that must be administered. The factors that may influence this choice include: the exact nature of the active and inactive ingredients included in the composition, the type of viral illness, the patient's condition, age, and weight, etc.

The following examples will demonstrate other characteristics and advantages of the present invention.

EXAMPLES

The examples which follow serve to illustrate the extent of the use of the present invention and not to limit its scope. Modifications and variations can be undertaken without escaping the spirit and scope of the invention. Although other methods and products equivalent to those found below can be used to test or carry out the present invention, the preferred materials and methods are described.

The reverse genetics systems used to obtain recombinant influenza viruses from cDNA clones are based on the transfection of plasmids that code for viral RNA (vRNA) under the control of the human RNA polymerase I promoter (Neumann et al., PNAS 96:9345-50, 1999; Fodor et al., J. Virol. 73:9679-82, 1999; Hoffman et al., PNAS 97:6108-13, 2000). The use of this promoter is justified by the fact that the ends of the transcription products should not contain additional nucleotides (if this is the case, the transcription/replication signals located at the non-coding 5' and 3' ends of the vRNA will no longer function).

The use of the human RNA polymerase I promoter ensures that transcription is initiated at a precise site, and thus ensures the precision of the 5' end of the vRNA synthesized in the transfected cells. But because of the very narrow species-specificity of RNA polymerase I promoters (Heix and Grummt, Curr. Op. Gent. Dev. 5:652-56, 1995), this type of system can be applied only to cells of human or simian origin.

Figure 3:
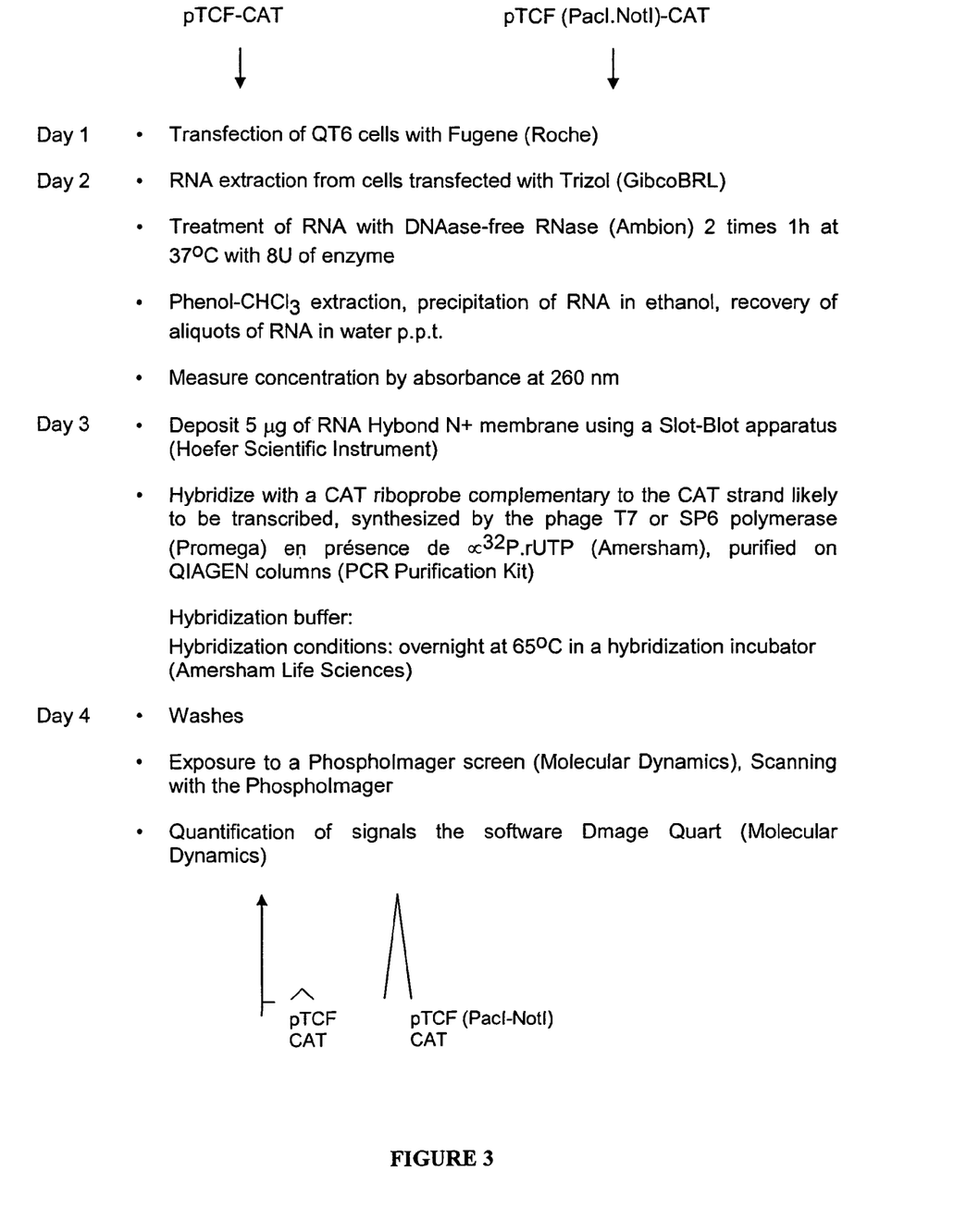
FIG. 3 shows the protocol used to analyze the efficiency of transcription of the CAT sequence using the sequences derived from C13-18 cosmid.
Figure 4:
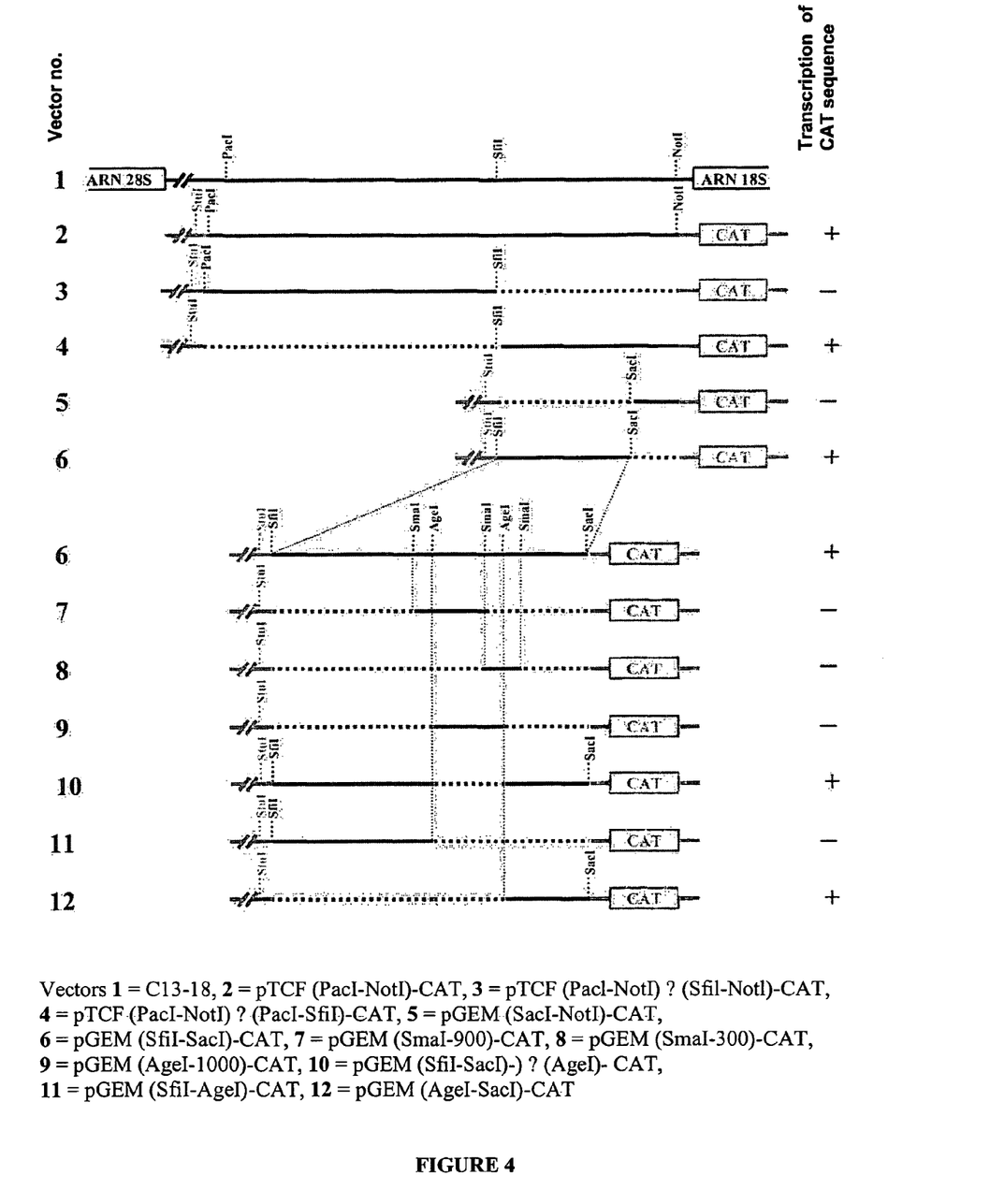
FIG. 4 shows the results of the iterative analysis of the restriction fragments derived from the PacI/NotI fragment derived from C13-18 cosmid.

However, the availability of a reverse genetics system appropriate for avian cells could open the way for the production of recombinant influenza vaccines in fertilized chicken eggs, which are the only medium currently authorized for the production of influenza vaccine in the United States. Today, vaccination constitutes the single means of influenza prevention, and it is strongly recommended for certain categories of subjects at risk. Production of the vaccine is based on the reproduction of vaccine strains in fertilized eggs, and requires with each new formulation the selection of reassortant viruses that have HA and NA segments representative of the strains in circulation, with the other segments being derived from a donor strain adapted to growth in eggs. It may be of advantage to replace this long and uncertain process with the production of virus reassortants by reverse genetics in fertilized eggs.

Thus, from the perspective of developing a recombinant influenza virus production system by reverse genetics in avian cells, the inventors undertook to clone the chicken RNA polymerase I promoter. Cloning by PCR based on the homologies between nucleotide sequences of the PolI promoters cloned to date was not possible because PolI transcription systems are widely divergent from one species to another. Thus, the inventors proceeded to screen the chicken genome.

1) Obtaining Cosmid C13-18

The mapping of the chicken genome indicated that the genes coding for ribosomal RNA (NOR locus) were located on chromosome 16, near the locus of the histocompatibility complex genes (Schmid et al., Cytogenet. Cell Genet., 90:169-218, 2000). In 1988, the laboratory of Professor H. Auffray, part of whose work at the Gustave Roussy Institute in Villejuif involves the major histocompatibility complex, published data concerning a recombinant cosmid (C13-18) which contained 30 kb of chicken genomic DNA, including major histocompatibility complex genes, but also several transcription units of the NOR locus and, consequently, at least one copy of the PolI promoter (Guillemot et al., EMBO J., 7:2775-85, 1988). This cosmid was graciously provided by R. Zoorob.

2) Southern Blot Analysis of C13-18 Cosmid

The C13-18 cosmid was analyzed by Southern blot after digestion by restriction enzymes NotI, PacI and SfiI, separately and in combination, and using as probes oligonucleotides chosen on the basis of the partial sequencing data for chicken ribosomal RNA available from the databanks:

```
oligonucleotide 28S/+/2:
5'-GAGTCAGCCCTCGACACAAGCTTTTG-3';    (SEQ ID NO: 3)

oligonucleotide 18S/-/1.5:
5'-CTACTGGCAGGATCAACCAGGT-3';        (SEQ ID NO: 4)
and oligonucleotide 18S/-/4:
5'-TAGAGGAGAACGCGACCTCGAGAC-3'.      (SEQ ID NO: 5)
```

This analysis made it possible to construct a rough restriction map of the C13-18 cosmid and to position the 18S and 28S ribosomal RNA with respect to the variety of restriction sites located on the cosmid. It also led to the identification of an approximately 16 kb PacI-NotI fragment, corresponding to the majority of an intergenic region and, by consequence, highly likely to contain a copy of the PolI promoter sequence.

3) Cloning the PacI-NotI Restriction Fragment Into a "Reporter" Vector and Demonstrating the Presence of a Transcriptional Promoter Within the PacI-NotI Fragment In order to test for the presence of the PolI promoter sequence within the PacI-NotI restriction fragment, the inventors sought to clone this restriction fragment upstream of a reporter sequence.

For this purpose, the pTCF cosmid (Grosveld et al., 1982, Nucleic Acids Res., 10, 6715-32), which has a single SalI cloning site, was modified by inserting into the SalI site a synthetic sequence that contained multiple cloning sites (StuI-PacI-NotI-PmeI).

The 16 kb PacI-NotI fragment derived from C13-18 was cloned into the modified pTCF cosmid, at the newly introduced PacI and NotI sites. Two pTCF-(PacI-NotI) recombinant cosmid clones were selected (nos. 2.5 and 2.7). Then a 500 bp EaeI restriction fragment derived from the bacterial chloramphenicol acetyl transferase (CAT) gene was cloned into the NotI site on the pTCF-(PacI-NotI) cosmids, in one orientation and the other. Four recombinant cosmid clones were selected: no. 2.5.3 and no. 2.7.13 (CAT in+orientation), no. 2.5.4 and no. 2.7.16 (CAT in−orientation).

In order to test for the presence of the PolI promoter sequence within the PacI-NotI restriction fragment, cells from the QT6 quail fibrosarcoma line were transfected with pTCF-(PacI-NotI)-CAT(+) and pTCF-(PacI-NotI)-CAT(−) cosmids. RNA was extracted from the cells 24 hours after transfection using the reagent TriZol (Gibco-BRL) and then treated with DNase (RNase-free DNase, Ambion) in order to eliminate the cosmid molecules that can contaminate RNA preparations. RNAs were deposited at 5 μg per point on a nylon membrane (Hybond N+, Amersham), and hybridized with a $^{32}P$-labeled riboprobe corresponding to the CAT (+) sequence. Positive signals were obtained with the RNA prepared from cells transfected with pTCF-(PacI-NotI)-CAT(−) cosmids nos. 2.5.4 and 2.7.16, which suggests the presence of a transcriptional promoter in the PacI-NotI restriction fragment. In these first experiments, nevertheless, the background signal-to-noise ratio was rather low. It was improved in the following experiments after optimizing the RNA treatment. conditions in DNase (twice for 1 hour at 37° C. in the presence of 8 units of enzyme) and the hybridization and membrane washing conditions (hybridization overnight at 65° C. in a buffer of 50% formamide, 5×SSC, 5× Denhart's, 0.5% SDS; 2 washings of 10 min. at ambient temperature in a buffer of 2×SSC, 0.1% SDS, followed by 2 washings of 10 min. at 65° C. in a buffer of 0.2×SSC, 0.1% SDS). The methodology, which was then applied in an iterative manner to examine the presence of a transcriptional promoter in the restriction fragments derived from the PacI-NotI fragment, is summarized in FIG. 3. The results obtained are detailed below and are summarized in FIG. 4.

4) Creating Partial Deletions within the Cloned PacI-NotI Restriction Fragment of the Reporter Vector and Demonstrating the Presence of a Transcriptional Promoter in an Approximately 6 kb SfiI-NotI Fragment In order to identify more precisely the region of the PacI-NotI fragment that contained the promoter, partial deletions of the Pacd-NotI fragment were obtained by digesting cosmids pTCF-(PacI-NotI)-CAT(−) no. 2.7.16 and pTCF-(PacI-NotI)-CAT(+) no. 2.7.13 with the enzyme combinations PacI-SfiI and SfiI-NotI (the SfiI site being located within the PacI-NotI fragment), filling-in the ends using the Kleenow sub-unit of E. coli PolI DNA, and religating the molecules obtained to themselves. The presence of a transcriptional promoter within the deleted cosmids was tested using the methodology described above (transfection of QT6 cells and analysis of the RNA extracted from the transfected cells by hybridization with a CAT probe). The results obtained suggested that a transcriptional promoter was present in the cosmids that had retained the SfiI-NotI portion (approximately 6 kb) of the Pacd-NotI fragment.

5) Iterative Analysis of the Restriction Fragments Derived From the SfI-NotI Fragment and Demonstrating the Presence of a Transcriptional Promoter in a 1200 bp AgeI-SacI Fragment In order to continue the analysis of restriction fragments derived from the SfiI-NotI fragment following the same methodology, a new reporter vector was constructed at this stage. Indeed, the restriction fragments analyzed were still of sufficiently reduced size to be able to be cloned into a plasmid.

This new reporter vector was constructed from the plasmid pGEM-5-zf+ (Promega), in which the 500 bp EaeI fragment derived from the bacterial CAT gene was cloned in orientation (+) at the single NotI site. Only this orientation of the CAT sequence in the reporter vector was used because the preceding experiments had indicated that the CAT (+) reporter sequence/CAT (−) riboprobe pair gave results that were more specific and reproducible than the CAT (−) reporter sequence/CAT (+) riboprobe pair.

The SfiI-SacI restriction fragments (in practice, a StuI-SacI fragment that includes the SfiI-SacI fragment) and the SacI-NotI restriction fragments derived from the SfiI-NotI fragment were subcloned into the EcoRV site of the pGEM-CAT (+) vector (clone no. 9), which is located upstream of the CAT reporter sequence. By the methodology described above, the presence of a transcriptional promoter was demonstrated in the StuI-SacI fragment cloned into the plasmid pGEM-(StuI-SacI)-CAT(+) (clone no. 12).

A restriction map of the StuI-SacI fragment was established based on pGEM-(StuI-SacI)-CAT(+) no. 12 plasmid digestions by SmaI and AgeI restriction enzymes. Two SmaI-SmaI restriction fragments, an AgeI-AgeI restriction fragment, and the StuI-SacI fragment deleted from this AgeI-AgeI restriction fragment were subcloned into the vector pGEM-CAT(+) no. 9 at the EcoRV site. The presence of a transcriptional promoter was demonstrated in the StuI-SacI fragment deleted from the AgeI-AgeI fragment, cloned into the plasmid known by convenience as V12-AgeI (clone no. 29).

The deleted StuI-SacI fragment was cut into two fragments, StuI-AgeI and AgeI-SacI, obtained by digesting plasmid V12-AgeI no. 29 with the NcoI+AgeI restriction enzymes on the one hand (for the StuI-AgeI fragment), and AgeI+NotI on the other hand (for the AgeI-SacI fragment). Each of the two fragments was subcloned into the pGEM-CAT(+) vector at the EcoRV site. The presence of a transcriptional promoter was demonstrated in the 1200 bp AgeI-SacI fragment, cloned into the plasmid pGEM-(AgeI-SacI)-CAT(+) (clone no. 15).

6) Sequencing the AgeI-SacI Fragment and Determining the Transcription Initiation Point by the Primer Extension Technique The AgeI-SacI fragment cloned into the plasmid pGEM-(AgeI-SacI)-CAT(+) no. 15 was sequenced. The sequence is represented in FIG. 1 (SEQ ID NO: 1).

The 800 bp distal to this sequence contain 8 repetitions of a sequence of approximately 90 nucleotides, which is characteristic of PolI promoters: indeed, the presence of repeated activating sequences upstream of the transcription initiation site was described for several PolI promoters derived from other species (Paule M., 1998, Promoter Structure of Class I Genes. In *Transcription of Ribosomal RNA Genes by Eukaryotic RNA Polymerase I*. Edited by M. R. Paule: Springer-Verlag and R.G. Landes Company).

The precise site of chicken PolI promoter transcription initiation was thus sought in the 400 bp proximal to the AgeI-SacI fragment, by the primer extension technique. An oligonucleotide complementary to the CAT sequence transcribed from the plasmid pGEM-AgeI-SacI)-CAT(+) (sequence SEQ ID NO: 6: 5'-ATGTTCTTTACGATGCGAT-TGGG-3') was labeled with $^{32}P$ at its 5' end using T4 phage polynucleotide kinase (Biolabs) and used in two parallel reactions: 1) as primed for the extension of a DNA complementary to the CAT RNA extracted from QT6 cells transfected with the plasmid pGEM-(AgeI-SacI)-CAT(+) no. 15 in the presence of reverse transcriptase (SuperScript II, Invitrogen), and 2) as primed for the sequencing of the plasmid pGEM-(AgeI-SacI)-CAT(+) no. 15 using a "T7 Sequencing Kit" (Pharmacia Biotech). A single transcription product was detected in the primer extension reaction, confirming the existence of a very precise transcription initiation site. This site was located in a region rich in A and T, in agreement with the data available for PolI promoters derived from other species, approximately 200 bp from the oligonucleotide used as a primer.

Figure 5:
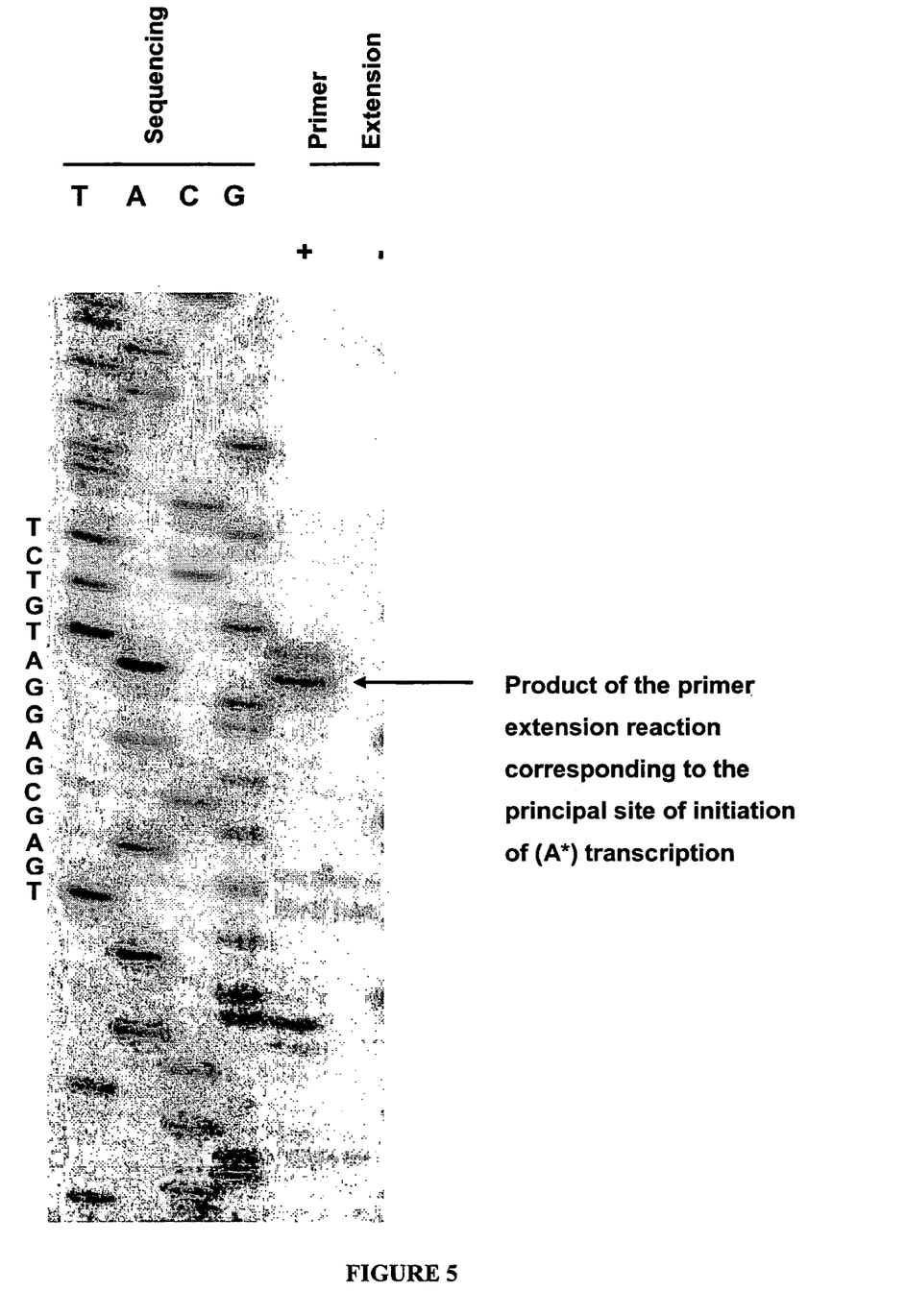
FIG. 5 shows the results of sequencing and primer extension reactions carried out in parallel, which demonstrate, within the AgeI/SacI fragment described in FIG. 1, the primary site for the initiation of transcription by chicken RNA polymerase I.

In parallel, the analysis of restriction fragments derived from the AgeI-SacI fragment was pursued in order to delimit the minimal promoter (which corresponds to a region of approximately 250 bp for the PolI promoters of other species) (see FIG. 5). The AgeI-SacI fragment was cut into three fragments, AgeI-BsaI, BsaI-BsaI, and BsaI-SacI, obtained by digesting the plasmid pGEM-(AgeI-SacI)-CAT(+) no. 15 with restriction enzymes NcoI+BsaI on the one hand (for the AgeI-BsaI and BsaI-BsaI fragments), and BsaI+NotI on the other hand (for the BsaI-SacI fragment). Each of the two fragments was subcloned into the pGEM-CAT(+) vector at the EcoRV site. Only the approximately 600 bp BsaI-SacI fragment (FIG. 2), cloned into the plasmid pGEM-(BsaI-SacI)-CAT(+) (clone no. 16), allowed the transcription of the CAT reporter sequence, which is perfectly consistent with the fact that it was the proximal fragment in which the transcription initiation site was located.

The nucleotide +1 to the transcription initiation site was determined by the primer extension technique, using an oligonucleotide located about fifty base pairs downstream from the initiation region (see FIG. 5). This oligonucleotide of sequence SEQ ID NO: 7 (5'-GGCCGGTCAACCCTGCTC-3') was labeled with $^{32}P$ at its 5' end using T4 phage polynucleotide kinase (Biolabs) and was used in two parallel reactions: 1) as primed for the extension of a DNA complementary to the CAT RNA extracted from QT6 cells transfected with the plasmid pGEM-(AgeI-SacI)-CAT(+) no. 15 in the presence of reverse transcriptase (SuperScript II, Invitrogen), and 2) as primed for the sequencing of the plasmid pGEM-(AgeI-SacI)-CAT(+) no. 15 using a "T7 Sequencing Kit" (Pharmacia Biotech). A majority transcription product was detected, corresponding to an initiation site that possesses a characteristic nucleotide environment (nucleotides underlined below) of the consensus sequence established from the PolI promoter sequences of other species:

The plasmid pPR7-C16-CAT-Rz contains nucleotides −1 to −425 of the chicken PolI promoter, whereas the plasmid pPR7-ΔC16-CAT-Rz contains only nucleotides −1 to −246 (for other species, the minimal size of the PolI promoter was estimated at approximately 250 nucleotides).

The plasmids PolI-CAT-Rz (human PolI promoter), pPR7-C16-CAT-Rz, and pPR7-ΔC16-CAT-Rz (avian PolI promoter) were transfected into avian QT6 cells and primate COS-1 cells simultaneously with plasmids coding for influenza virus proteins PB1, PB2, PA, and NP. If the transfected cells simultaneously express the correct pseudo-influenza RNA at the non-coding 5' and 3' ends and proteins PB1, PB2, PA and NP, the pseudo-influenza RNA can be transcribed and replicated, and the efficacy of the transcription/replication process can be estimated by measuring the level of CAT protein in the transfected cells. Thus, CAT protein levels in cytoplasmic extracts from the transfected cells were measured by ELISA, prepared 24 hours post-transfection.

Figure 6:
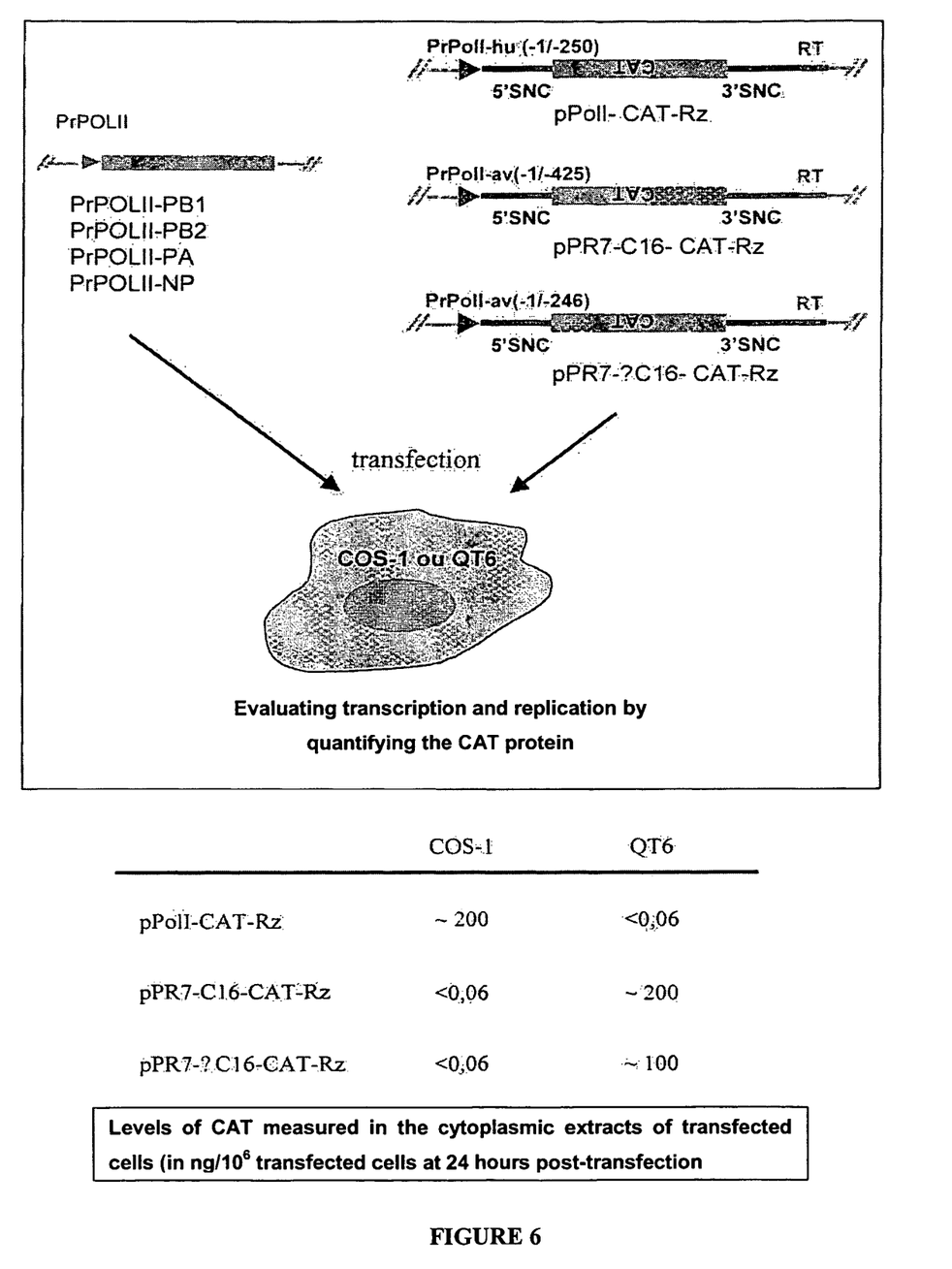
FIG. 6 is a diagram that shows the CAT levels measured in the cytoplasmic extracts of cells transfected with plasmids coding for pseudo influenza RNA under the control of human or chicken PolI promoters (in ng/10$^6$ of transfected cells at the sequence coding for bacterial chloramphenicol acetyl transferase (CAT) was cloned into the NotI site of pGEM52F+. An AgeI-SacI restriction fragment derived from a C13-18 cosmid was cloned into the pGEM5F+ EcoRI site, upstream from the CAT insert. This 1260 bp fragment contains the minimal chicken RNA polymerase I promoter of the present invention.

The CAT levels measured in the presence of the plasmid pPolI-CAT-Rz were on the order of 200 ng/$10^6$ transfected COS-1 cells, whereas they were very low (<0.06 ng/$10^6$ transfected cells) with respect to the QT6 cells (FIG. 6).

```
                         +1
TTATATGTTCGTC T G T* A G G A G C G A G T G A G* G* ACTCGGCT.    (SEQ ID NO: 8)
```

It should be noted, however, that three other minority transcription product types were detected in this primer extension experiment, corresponding to initiations at nucleotides −1, +13, and +14 (nucleotides above marked with an asterisk).

Plasmids intended to express a pseudo-influenza RNA carrying the CAT gene reporter sequence under the control of the chicken PolI promoter were constructed on the model of plasmid pPolI-CAT-Rz designed by Pleschka et al. using human PolI promoter (1996, J. Virol., 70:4188-92): these plasmids (pPR7-C16-CAT-Rz and pPR7-ΔC16-CAT-Rz) contain the sequences coding for the CAT gene, cloned in the anti-sense, and flanked by non-coding 5' and 3' sequences derived from the NS gene segment of a human Type A influenza virus; positioning the non-coding 5' end downstream from nucleotide −1 of the chicken PolI promoter, on the one hand, and inserting the hepatitis δ virus ribozyme sequence at the 3' non-coding end, on the other hand, are intended to ensure the precision of the ends of the transcription product.

On the contrary, the CAT levels measured in the presence of plasmids pPR7-C16-CAT-Rz and pPR7-ΔC16-CAT-Rz were very low (<0.06 ng/$10^6$ transfected cells) in COS-1 cells, but the levels were on the order of 200 and 100 ng/$10^6$ cells, respectively, in QT6 cells (FIG. 6).

These results establish that the chicken PolI promoter sequences cloned into plasmids pPR7-C16-CAT-Rz and pPR7-ΔC16-CAT-Rz allow, after transfection into cells of avian origin, the transcription in vivo of mini-replicons that contain influenza virus Type A replication signals. Thus, they open the way for the development of reverse genetics systems that make it possible to obtain recombinant influenza viruses from avian cells in culture, or directly in fertilized chicken eggs.

The invention claimed is:

1. An isolated or purified polynucleotide, which comprises a sequence having a transcription promoting activity, selected from:
   a) SEQ ID NO: 1;
   b) a fragment of SEQ ID NO: 1 comprised of the nucleotide at the 5' terminus of SEQ ID NO: 8 and the approximately 250 nucleotides of SEQ ID NO: 1 consecutively and immediately upstream of the nucleotide at the 5' terminus of SEQ ID NO: 8;
   c) SEQ ID NO: 2;
   d) a fragment of SEQ ID NO: 1 comprised of the −1transcription initiation site of SEQ ID NO: 8 and the approximately 250 of SEQ ID NO: 1nucleotides consecutively and immediately upstream of the −1 transcription initiation site;
   e) a fragment of SEQ ID NO: 1and the approximately 250 nucleotides of SEQ ID NO: 1 consecutively and immediately upstream of the −1 transcription initiation site of SEQ ID NO: 8;
   f) a fragment of SEQ ID NO: 1 and the approximately 250 nucleotides of SEQ ID NO: 1 consecutively and immediately upstream of the +13 transcription initiation site of SEQ ID NO: 8;
   g) a fragment of SEQ ID NO: 1and the approximately 250 nucleotides of SEQ ID NO: 1 consecutively and immediately upstream of the +14 transcription initiation site of SEQ ID NO: 8; and
   (h) a sequence having at least 90% identity to a sequence in a) through g).

2. An isolated or purified polynucleotide, which comprises a sequence having a transcription promoting activity, selected from:
   a) a fragment of SEQ ID NO: 1 comprised of the approximately 250 nucleotides of SEQ ID NO: 1 consecutively and immediately upstream from the −1 transcription initiation site of SEQ ID NO: 8;
   b) a fragment of SEQ ID NO: 1 comprised of the approximately 250 nucleotides of SEQ ID NO: 1 consecutively and immediately upstream from the +13 transcription initiation site of SEQ ID NO: 8;
   c) a fragment of SEQ ID NO: 1 comprised of the approximately 250 nucleotides of SEQ ID NO: 1 consecutively and immediately upstream from the +14 transcription initiation site of SEQ ID NO: 8;
   d) a fragment of SEQ ID NO: 1 comprised of the −1transcription initiation site of SEQ ID NO: 8 and the approximately 425 nucleotides consecutively and immediately upstream from the −1 transcription initiation site; and
   e) a sequence having at least 90% identity to a sequence in a) through e).

3. A polynucleotide in accordance with claim 1, contained in the strain pGEM-ChPolI-C15-*E. Coli* 1305 deposited with the Collection Nationale de Cultures de Micro-organisms (CNCM) under number I-2976.

4. An isolated or purified polynucleotide as claimed in claim 2, comprising the nucleotides from approximately −1 to −246 of SEQ ID NO: 1 contained in plasmid pGEM-ChPolI-C15, which is contained in strain pGEM-ChPolI-C15-*E. coli* 1305 deposited at C.N.C.M. under Accession No. I-2976 on Feb. 24, 2003.

5. A recombinant DNA comprising a polynucleotide in accordance with claim 1 or claim 2.

6. A recombinant DNA in accordance with claim 5, which comprises a sequence to be transcribed.

7. A recombinant DNA in accordance with claim 6, wherein the sequence to be transcribed is cDNA of an uncapped RNA virus.

8. A recombinant DNA in accordance with claim 7, wherein the uncapped RNA virus is a negative-polarity RNA virus.

9. A recombinant DNA in accordance with claim 8, wherein the negative-polarity RNA virus is an orthomyxovirus or a paramyxovirus.

10. A recombinant DNA in accordance with claim 9, wherein the orthomyxovirus is an influenza virus.

11. A recombinant DNA in accordance with claim 9, which expresses a vRNA of an orthomyxovirus.

12. A recombinant DNA in accordance with claim 9, wherein the paramyxovirus is selected from among the genus *Rubulavirus*, the genus *Morbillivirus*, the genus *Pneumovirus*, and the genus *Metapneumovirus*.

13. A vector comprising a recombinant DNA in accordance with claim 5.

14. An isolated avian host cell comprising a recombinant DNA in accordance with claim 5.

15. An isolated avian host cell in accordance with claim 14, wherein the isolated avian host cell is an isolated poultry cell.

16. An isolated fertilized avian egg comprising a recombinant DNA in accordance with claim 5.

17. A composition comprising a pharmaceutically acceptable vehicle comprising the polynucleotide in accordance with claim 1 or claim 2.

18. A recombinant DNA in accordance with claim 11, wherein the vRNA is chosen from among influenza virus vRNA segments 1 to 8.

19. A method for producing a recombinant influenza virus by reverse genetics, comprising:
  a) introducing into an isolated avian cell or isolated fertilized avian egg one or several vectors comprising a recombinant DNA in accordance with claim 5 and vectors that express influenza virus proteins PA, PB1, PB2, and NP;
  b) culturing or incubating the isolated avian cell or isolated fertilized avian egg obtained in a) under conditions that make possible the expression of a recombinant influenza virus; and
  c) recovering the recombinant influenza virus obtained in b).

20. A method in accordance with claim 19, wherein the isolated avian cell is an isolated chicken cell.

21. A method in accordance with claim 19, wherein the recombinant influenza virus is Type A.

* * * * *

UNITED STATES PATENT AND TRADEMARK OFFICE
CERTIFICATE OF CORRECTION

| | |
|---|---|
| PATENT NO. | : 7,935,807 B2 |
| APPLICATION NO. | : 10/547155 |
| DATED | : May 3, 2011 |
| INVENTOR(S) | : Naffakh et al. |

It is certified that error appears in the above-identified patent and that said Letters Patent is hereby corrected as shown below:

Title page, item (73), lines 2-4,
"Centre National de la Recherche Scientifique (SNRS)" should read
--Centre National de la Recherche Scientifique (CNRS)--.

Claim 1, col. 19, line 29,
"SEQ ID NO: 1nucleotides" should read
--SEQ ID NO: 1 nucleotides--.

Claim 1, col. 19, line 40,
"SEQ ID NO: 1and" should read
--SEQ ID NO: 1 and--.

Claim 2, col. 19, lines 63-64,
"the -1transcription" should read
--the -1 transcription--.

Signed and Sealed this
Sixteenth Day of August, 2011

David J. Kappos
*Director of the United States Patent and Trademark Office*

SEQUENCE LISTING

<160> NUMBER OF SEQ ID NOS: 8

<210> SEQ ID NO 1
<211> LENGTH: 1261
<212> TYPE: DNA
<213> ORGANISM: Gallus gallus
<220> FEATURE:
<223> OTHER INFORMATION: Promoter sequence of the chicken RNA
      polymerase I

<400> SEQUENCE: 1

```
ccggtggtcc cggccccgtc cgactcggtc gcttcgcgga ggtggctgga ggtcgctgcc      60
gtggcggctg gggcacggcg gaacggtcta accggctccg gcgggccccg tccgcctcgg     120
tcgctgctcg gcggctgcta ggggtcgctg ccggggtggc tggggcacgg cggaacggtc     180
tacccgggtc cggcgggcgc cgtccggctc ggtcgctccg cggaggaggc taggggtcgc     240
tgccggggcg tctcggaaac ggcggaacgg tctaccccggc tccggcgggc cccgtccgcc     300
tcggtcgctc cgcgccggcg gcggctagag gtcgctgccg tgtcggctcg gaaacggcgg     360
aacggtctac ccggctccga cgggcgccgt ccggctcggt agctccgcgg cggcggctag     420
aggtcgctgc cgtgtcggct cggaaacggc ggaacggtct acccggctcc ggcgggcgcc     480
gtccggctcg gtctctccgc ggcggcggct agaggtcgct gccgtgtcgg ctcggaaacg     540
gcggaacggt ctacccgggt ccgacgggcg ccgtccggct cggtctctcc gcggcggcgg     600
ctagaggtcg ctgccgtgtc ggctcggaaa cggcggaacg gtctacccgg ctccgacggg     660
ccccgtccgg ctcggtcgct ccgcggcggc ggctaggggt cgctgccggg gcgtctcgga     720
aacggcggaa cggtctaccc gggtgctacc gactcgcgct ccgcgcgcg gcggctagag     780 gtcgctgccg gggcggcttg cgatccgcgt ccaggtctac ccggtttcgg attgtcttgg     840
ccgctctggc tgtggggggg ggcgctacag ctccggagct gccagaggcg tcgctgtaat     900
tttgtacctc cagttacgtc gaggtaaacc tcggctgccg tcggagccgc tgccggtagt     960
cggcgcctat ggggctagaa cgtttttttc ggatgcctta tatgttcgtc tgtaggagcg    1020
agtgaggact cggctccggt agtggcggtg agcgggcgct cgcgagcagg gttgaccggc    1080
cggccgccta gagaggggat cggcggcggc ggcggcggct ttctcgggca tcggttcgtt    1140
cgatcggtcc ggtcgcttcg gtttgtccgt cgctcctcat cccgcagctc tgtcctgggc    1200
taaggcggtt ttgcaggcga gcagcgaaaa aaagccggag aaggcgatca ctagtgcggc    1260
c                                                                   1261
```

<210> SEQ ID NO 2
<211> LENGTH: 674
<212> TYPE: DNA
<213> ORGANISM: Gallus gallus
<220> FEATURE:
<223> OTHER INFORMATION: Promoter sequence of the chicken RNA
      polymerase I

<400> SEQUENCE: 2

```
tccgcggcgg cggctagagg tcgctgccgt gtcggctcgg aaacggcgga acggtctacc      60
cggctccgac gggccccgtc cggctcggtc gctccgcggc ggcggctagg ggtcgctgcc     120
ggggcgtctc ggaaacggcg gaacggtcta cccgggtgct accgactcgc gctctccgcg     180
gcggcggcta gaggtcgctg ccggggcggc ttgcgatccg cgtccaggtc tacccggttt     240
cggattgtct tggccgctct ggctgtgggg ggggcgctac agctccgga gctgccagag     300
```

```
gcgtcgctgt aattttgtac ctccagttac gtcgaggtaa acctcggctg ccgtcggagc    360
cgctgccggt agtcggcgcc tatggggcta gaacgttttt ttcggatgcc ttatatgttc    420
gtctgtagga gcgagtgagg actcggctcc ggtagtggcg gtgagcgggc gctcgcgagc    480
agggttgacc ggccggccgc ctagagaggg gatcggcggc ggcggcggcg gctttctcgg    540
gcatcggttc gttcgatcgg tccggtcgct tcggtttgtc cgtcgctcct catcccgcag    600
ctctgtcctg ggctaaggcg gttttgcagg cgagcagcga aaaaaagccg gagaaggcga    660
tcactagtgc ggcc                                                      674

<210> SEQ ID NO 3
<211> LENGTH: 26
<212> TYPE: DNA
<213> ORGANISM: Artificial sequence
<220> FEATURE:
<223> OTHER INFORMATION: Oligonucleotide derived from chicken
      ribosomal RNA

<400> SEQUENCE: 3
gagtcagccc tcgacacaag cttttg                                         26

<210> SEQ ID NO 4
<211> LENGTH: 22
<212> TYPE: DNA
<213> ORGANISM: Artificial sequence
<220> FEATURE:
<223> OTHER INFORMATION: Oligonucleotide derived of chicken ribosomal
      RNA

<400> SEQUENCE: 4
ctactggcag gatcaaccag gt                                             22

<210> SEQ ID NO 5
<211> LENGTH: 24
<212> TYPE: DNA
<213> ORGANISM: Artificial sequence
<220> FEATURE:
<223> OTHER INFORMATION: Oligonucleotide derived from chicken
      ribosomal RNA

<400> SEQUENCE: 5
tagaggagaa cgcgacctcg agac                                           24

<210> SEQ ID NO 6
<211> LENGTH: 23
<212> TYPE: DNA
<213> ORGANISM: Artificial sequence
<220> FEATURE:
<223> OTHER INFORMATION: Complementary oligonucleotide of the CAT
      sequence transcribed from pGEM-(AgeI-SacI)-CAT(+) plasmid

<400> SEQUENCE: 6
atgttcttta cgatgcgatt ggg                                            23

<210> SEQ ID NO 7
<211> LENGTH: 18
<212> TYPE: DNA
<213> ORGANISM: Artificial sequence
<220> FEATURE:
<223> OTHER INFORMATION: Primer derived from promoter of the chicken
      RNA Polymerase I

<400> SEQUENCE: 7
ggccggtcaa ccctgctc                                                  18
```

```
<210> SEQ ID NO 8
<211> LENGTH: 38
<212> TYPE: DNA
<213> ORGANISM: Artificial sequence
<220> FEATURE:
<223> OTHER INFORMATION: oligonucleotide derived from a transcription
      product corresponding to an initiation site of the chicken RNA
      polymerase I promoter

<400> SEQUENCE: 8
ttatatgttc gtctgtagga gcgagtgagg actcggct                              38
```